United States Patent
Guala

(10) Patent No.: US 10,137,291 B2
(45) Date of Patent: Nov. 27, 2018

(54) VALVED CONNECTOR FOR MEDICAL LINES

(71) Applicant: INDUSTRIE BORLA S.P.A., Moncalieri (Turin) (IT)

(72) Inventor: Gianni Guala, Turin (IT)

(73) Assignee: INDUSTRIE BORLA S.P.A., Moncalieri (Turin) (IT)

( * ) Notice: Subject to any disclaimer, the term of this patent is extended or adjusted under 35 U.S.C. 154(b) by 206 days.

(21) Appl. No.: 15/115,396

(22) PCT Filed: Dec. 31, 2014

(86) PCT No.: PCT/IB2014/067444
§ 371 (c)(1),
(2) Date: Jul. 29, 2016

(87) PCT Pub. No.: WO2015/114428
PCT Pub. Date: Aug. 6, 2015

(65) Prior Publication Data
US 2017/0000998 A1    Jan. 5, 2017

(30) Foreign Application Priority Data
Jan. 31, 2014 (IT) ............... TO2014A0078

(51) Int. Cl.
*A61M 39/10* (2006.01)
*A61M 39/20* (2006.01)
*A61M 39/24* (2006.01)

(52) U.S. Cl.
CPC ............ *A61M 39/10* (2013.01); *A61M 39/20* (2013.01); *A61M 39/24* (2013.01);
(Continued)

(58) Field of Classification Search
CPC .......... A61M 2039/1033; A61M 39/10; A61M 39/26; A61M 2039/261; A61M 2039/262;
(Continued)

(56) References Cited

U.S. PATENT DOCUMENTS 5,032,116 A    7/1991 Peterson et al.
7,559,530 B2   7/2009 Korogi et al.
(Continued)

FOREIGN PATENT DOCUMENTS

EP    0081655 A1    10/1982
EP    1834665 A1    3/2007
(Continued)

OTHER PUBLICATIONS

Corresponding International Search Report and Written Opinion for corresponding International Application No. PCT/IB2014/067444 filed on Dec. 31, 2014, completed on Apr. 8, 2015 and dated Apr. 16, 2015.

*Primary Examiner* — Nathan R Price
*Assistant Examiner* — John Doubrava
(74) *Attorney, Agent, or Firm* — Heslin Rothenberg Farley & Mesiti P.C.

(57) ABSTRACT

A valved male luer connector includes an elastic hollow element which encloses a tubular member having an inlet portion and an outlet portion. A collar is axially displaceable causing a stretching deformation of the elastic hollow element and opening the flow passage between the inlet portion and the outlet portion of the tubular member. A priming cap is designed to be releasably connected to the casing of the valved connector to provide stretching deformation of the elastic element and keep the outlet portion of the tubular member in communication with the atmosphere through a liquid-impermeable barrier.

6 Claims, 4 Drawing Sheets

(52) U.S. Cl.
CPC ............. *A61M 2039/1027* (2013.01); *A61M 2039/1033* (2013.01); *A61M 2039/1072* (2013.01); *A61M 2039/205* (2013.01); *A61M 2039/2433* (2013.01); *A61M 2039/2473* (2013.01)

(58) Field of Classification Search
CPC ...... A61M 2039/263; A61M 2039/265; A61M 2039/266; A61M 2039/267; A61M 2039/268
See application file for complete search history.

(56) References Cited

U.S. PATENT DOCUMENTS

| | | | |
|---|---|---|---|
| 2005/0151105 A1* | 7/2005 | Ryan | A61M 39/26 251/149.6 |
| 2007/0156118 A1* | 7/2007 | Ramsey | A61M 39/20 604/533 |
| 2013/0079730 A1* | 3/2013 | Mosler | A61M 39/10 604/244 |

FOREIGN PATENT DOCUMENTS

| | | |
|---|---|---|
| WO | 2004014477 A1 | 2/2004 |
| WO | 2011064738 A2 | 6/2011 |

\* cited by examiner

VALVED CONNECTOR FOR MEDICAL LINES

CROSS-REFERENCE TO RELATED APPLICATIONS

This application is a 371 national stage of PCT International Application No. PCT/IB2014/067444, filed on Dec. 31, 2014, and published in English on Aug. 6, 2015 as WO 2015/114428 A1, which claims priority to Italian Patent Application No. TO2014A000078 filed on Jan. 31, 2014, the entire disclosures of which are incorporated herein by reference.

FIELD OF THE INVENTION

The present invention relates in general to connectors for medical fluids, and particularly concerns a valved male luer connector connectable to a fluid line and designed to be connected to a connector generally of the female luer type and the like to open the flow passage of the fluid through the two connectors.

STATE OF THE PRIOR ART

From the patent U.S. Pat. No. 7,559,530, as well as the European patent application EP-2504056 (WO-2011/064738), both owned by the Applicant, a valved male luer connector is disclosed, comprising a casing, a tubular member having an inlet portion and an outlet portion with an open terminal end, and an elastic hollow element secured to the casing and enclosing the tubular member. The elastic hollow element has a terminal wall, which normally seals closed the terminal end of the outlet portion of the tubular member and has a cut. A collar interposed between the casing and the elastic hollow element is axially displaceable, following thrust engagement by a female connector connectable to the male connector, causing a stretching deformation of the elastic hollow element elastic and consequent opening of the flow passage between the inlet portion and the outlet portion of the tubular member.

This valved male luer connector thus operates according to the stretching deformation of the elastic hollow element: in this way, it can guarantee a perfect closure in the absence of the female connector, a prompt opening during coupling with the female connector, and a rapid return to the closed condition following decoupling of the female connector.

In the case where the tubular member is connected to a supply line of a medical liquid contained, for example, in a bag, it is necessary to carry out "priming" of the line beforehand, or rather before the connection of the female connector for transferring the medical liquid to a patient. Therefore, the operator must manually open the valved connector until the medical liquid coming from the line reaches the terminal end of the tubular member. This operation is delicate and can be complicated and inconvenient.

From the documents U.S. Pat. No. 5,032,116A and WO-2004/014477, medical devices provided with a removable ventilation cap are known.

SUMMARY OF THE INVENTION

The object of the present invention is to resolve the aforesaid problem in a simple, practical and functional manner and in a manner to avoid losses of liquid.

According to the invention, this object is achieved thanks to a valved male luer connector of the type defined at the beginning, and corresponding to the preamble of claim 1, whose unique characteristic lies in the fact that it includes a priming cap, designed to be releasably connected to the connector casing for stretching deformation of said elastic element, and to keep said terminal end of the outlet portion of the tubular member in communication with the atmosphere by means of a liquid-impermeable membrane. The priming cap comprises a skirt arranged on the outside of the casing and configured to engage the connector casing and a tubular part coaxial to the skirt, which on one side carries the aforesaid liquid-impermeable barrier and on the opposite side it is arranged to interact with the collar interposed between the casing and the elastic hollow element.

The skirt of the priming cap is selectively engageable with said casing, in a first axial position to protect the end wall of the elastic hollow element, in which this elastic hollow element is essentially undeformed, and in a second axial position in which said elastic hollow element is stretched.

In the second axial position, the skirt of the priming cap is conveniently connected to the casing of the connector by means of a bayonet coupling.

Thanks to this solution idea, the valved male luer lock connector according to the invention enables, during use, the immediate connection to the female connector without the need of firstly having to perform priming of the supply line of the medical liquid, since the priming is made ready and available by the presence of the cap applied in a removable manner to the body of the connector, without the risk of liquid loss, when it is arranged in the aforesaid second axial position. The connection of the valved male luer lock connector to the female connector can therefore be carried out directly, following removal of the priming cap, the effect of which returns the elastic element to the undeformed closed condition of the connector, which will then be reopened due to the effect of coupling with the female connector.

BRIEF DESCRIPTION OF THE DRAWINGS

Further characteristics and advantages of the invention will become apparent from the detailed description which follows, with reference to the attached drawings provided purely by way of non-limiting example, in which.

DETAILED DESCRIPTION OF THE INVENTION

Figure 1:
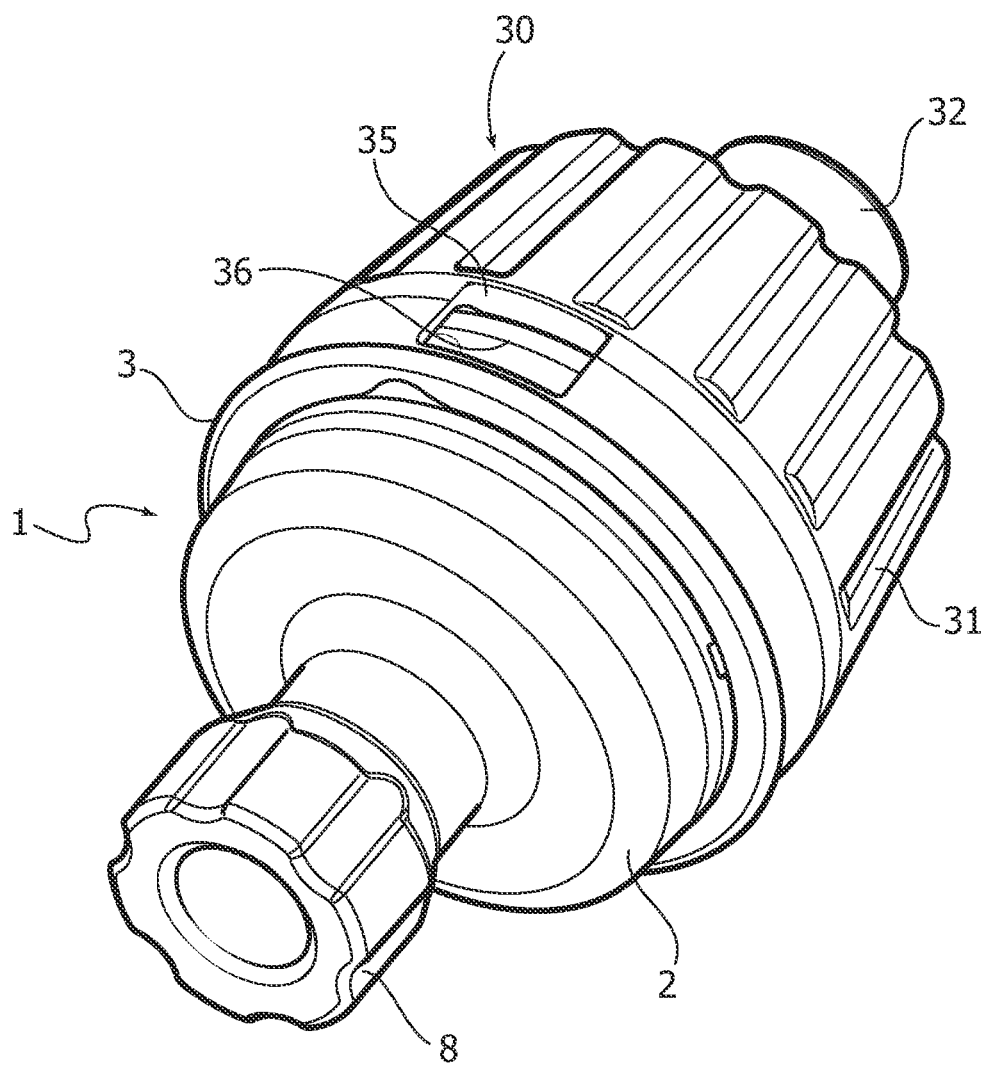
FIG. 1 is a schematic perspective view of the valved male luer connector according to the invention.

Referring to the drawings, the valved male luer connector according to the invention comprises (in a generally known manner from the aforementioned documents U.S. Pat. No. 7,559,530 and EP-2504056), a casing 1 formed of a lower flange portion 2, permanently coupled to an upper hollow body 3 formed, at the opposite side to the flange 2, of an internally threaded seat 4.

The flange 2 is, in turn, formed integrally and coaxially with a tubular member indicated as a whole by 5, having an inlet portion 7 and an outlet portion 6, which extends through the hollow body 3 and projects outwards from the relative threaded seat 4. The outlet portion 6, together with other parts that will be described below, defines with the threaded seat 4, a male luer lock connector suitable for engagement with a female connector, not illustrated as it is a per se known type. For example, the female connector can be of the valved type described and illustrated in the document EP-1834665, also by the Applicant.

The inlet portion 7 communicates with a tubular appendage 8, which is also integrally formed with the flange 2 and protrudes at the rear of the casing 1, for example, configured for attachment of a flexible line connected to a bag containing a medical liquid for infusion.

The inlet portion 7 and the outlet portion 6 are connected to each other by means of two series of separate passages 9, 10 whose mutual communication is controlled in the manner explained below.

The outlet portion 6 of the tubular member 5 has one open terminal end, indicated by 11, at which an annular enlargement 12 is formed, which defines the upper limit of an outer annular groove 13, in turn having a lower limit defined by a stop step 14.

Numeral 15 indicates an elastic hollow element, typically made of elastomeric rubber or silicone, including an annular base 16 secured to the casing 1 between the flange 2 and the body 3, a generally cylindrical first part 17 connected to the base 16 by means of a generally conical part 18 diverging towards this first cylindrical part 17, and a second generally cylindrical part 19, slightly narrower than the first cylindrical part 17 and having a terminal transverse wall 20.

The terminal wall 20 has a central cut 21, for example, linear or of tricuspid form, as in the case of the example illustrated, which is normally closed due to the intrinsic elasticity of the elastic hollow element 15 in order to essentially seal closed the open terminal end 11 of the tubular member 5.

The second cylindrical portion 19 of the elastic hollow element 15 is internally formed with an annular guiding protrusion 23, slidable within the groove 13 of the inlet portion 6 of the tubular member 5, between the annular enlargement 12 and the step 14.

The first cylindrical part 17 of the elastic hollow element 15 has, internally, a first, a second and a third annular sealing protrusion axially spaced apart from each other, indicated respectively by 24, 25 and 26 and in slidable sealing contact on the tubular member 5. The annular protrusion 24 interacts with the passages 9 and 10 to close and open, respectively, the communication between the inlet portion 7 and the outlet portion 6 of the tubular member 5. In the condition represented in FIG. 2, the passages 9 and 10 are isolated from each other by the annular sealing protrusion 24, while in the condition represented in FIG. 5, passages 9 and 10 are in communication.

The reference 28 indicates a collar interposed between the hollow body 3 of the casing 1 and the elastic hollow element 15, forming an actuator member, configured for controlling the opening of the flow passage through the connector due to a stretching deformation of the elastic hollow element 15. The collar 28 has an outer annular step 29, arranged to cooperate, in the manner described in the aforementioned document EP-2504056, with a female luer connector or the like, coupled in the seat 4 of the body 3. As a result of this coupling, the female connector applies an axial thrust against the step 29 of the collar 28 in order to push it in the direction of the inlet portion 7 of the tubular member 5 and to elastically deform the elastic hollow element 15 in order to open the flow passage between the tubular appendage 8 and the female connector through the terminal end 11 of the outlet portion 6 of the tubular member 5, in the manner represented in FIG. 5 which will be discussed below.

According to the unique characteristic of the invention, the valved male luer connector is also equipped with a priming cap, indicated as a whole by 30, which is designed to be releasably connected to the casing 1 to keep the connector in a condition of at least partial opening before its coupling with the female connector. In this way, during use, the medical liquid coming from the line connected to the tubular appendage 8 is able to reach the terminal end 11 of the tubular member 5 without the need for a priming intervention by the operator, thus rendering the valved male luer connector ready for its coupling to the female connector for the supply of medical liquid to a patient.

The priming cap 30 comprises a ridged skirt 31, configured in order to externally enclose the hollow body 3 of the connector, and a tubular part coaxial to the skirt 31 and having an outer portion 32 projecting axially beyond the skirt 31 and an inner portion 33 protruding inside this skirt 31. The outer portion 32 carries a transversal liquid-impermeable barrier, typically formed of a hydrophobic membrane 34, while the inner portion 33 is configured to interact with the step 29 of the collar 28.

Figure 2:
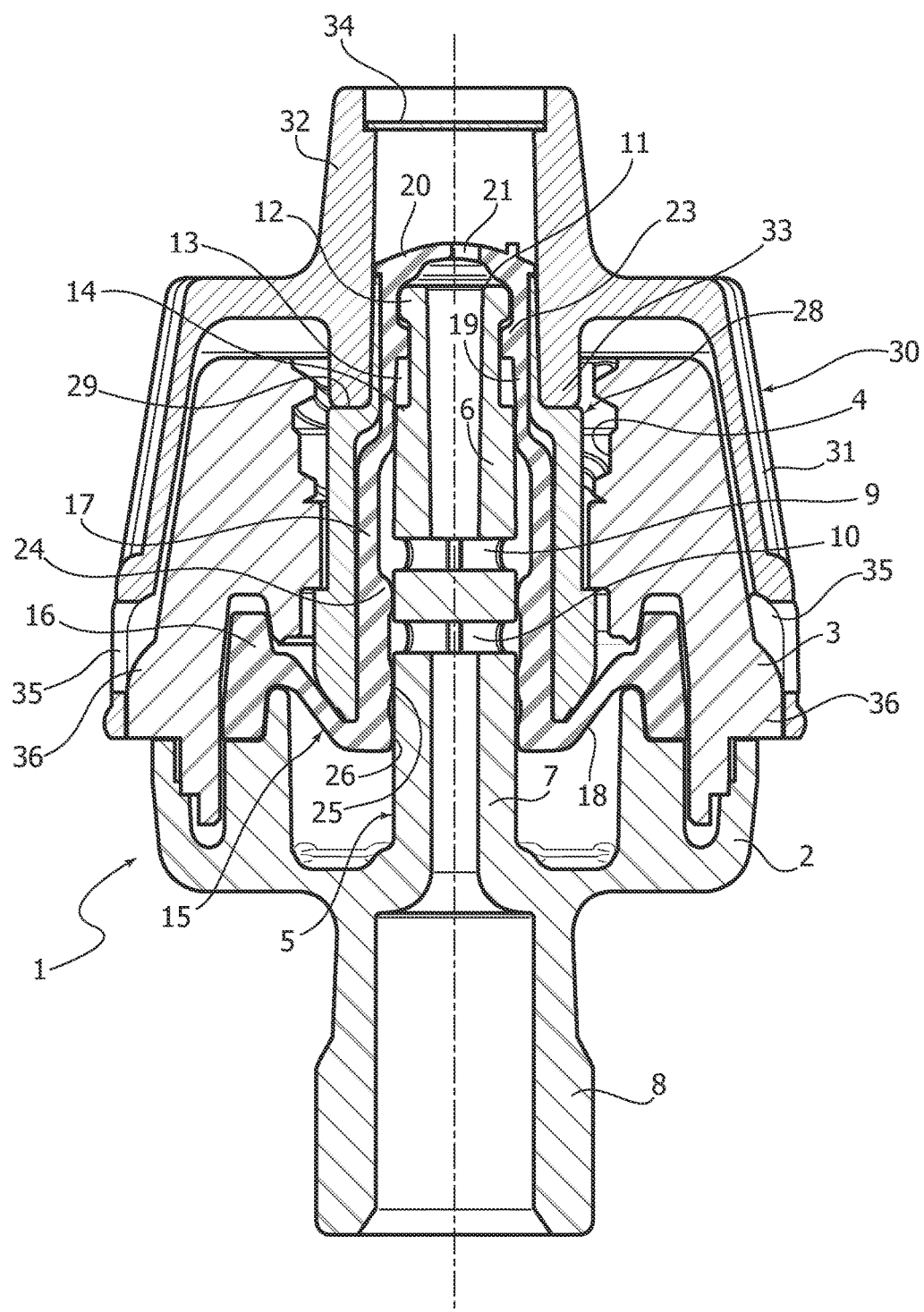
FIG. 2 is a view in axial cross-section of the valved connector in a first condition.
Figure 3:
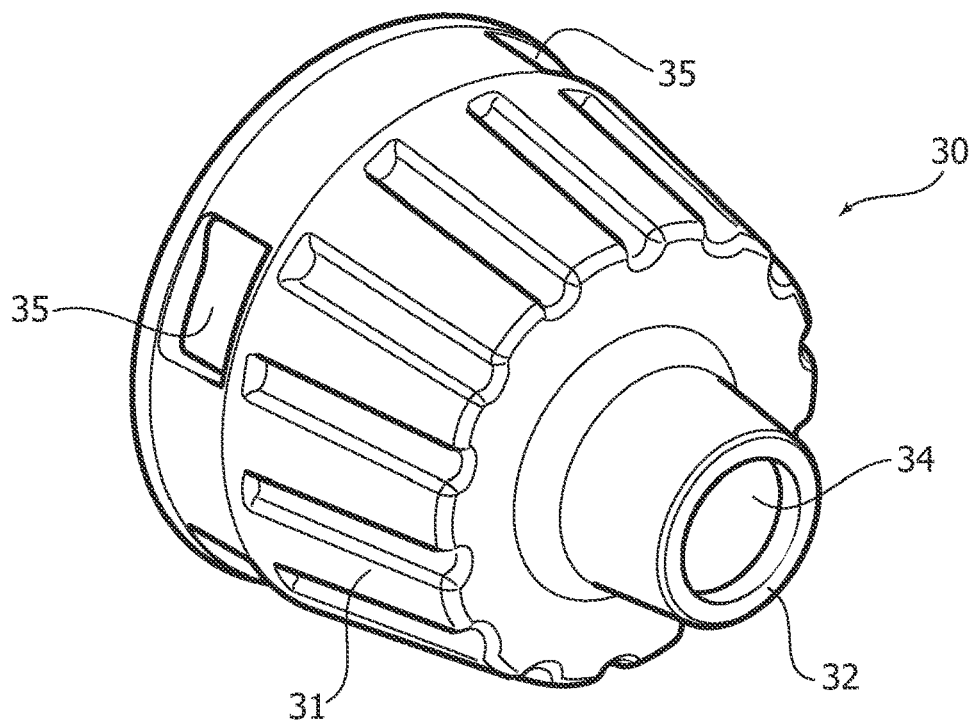
FIGS. 3 and 4 are two perspective views, frontal and dorsal, respectively, of the priming cap of the valved connector according to the invention.
Figure 4:
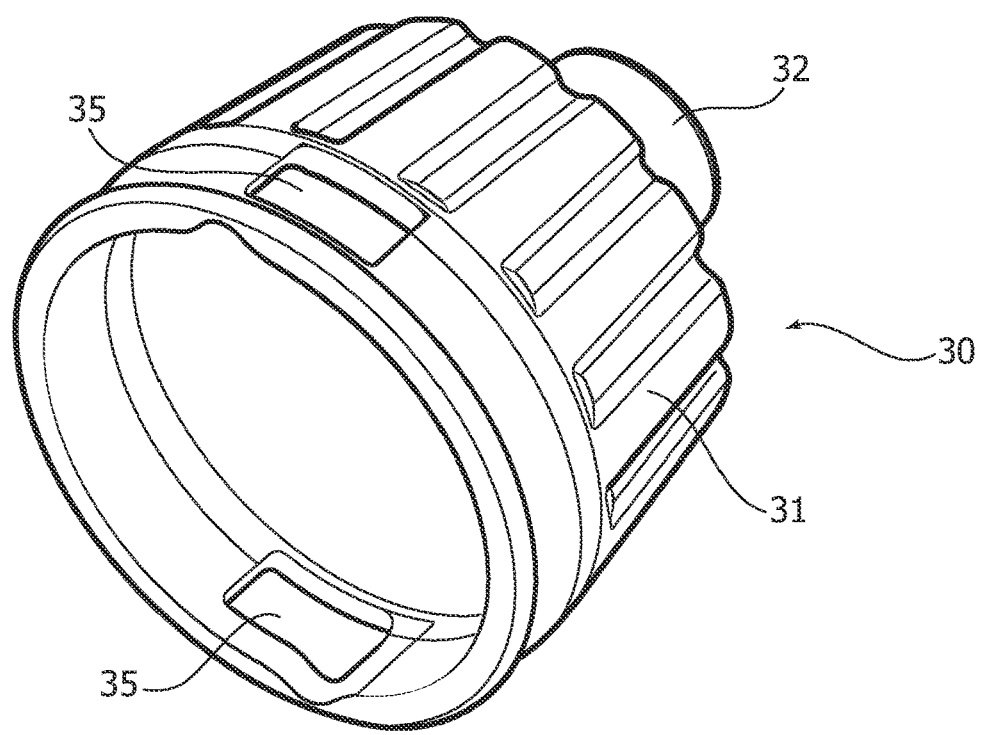
Figure 5:
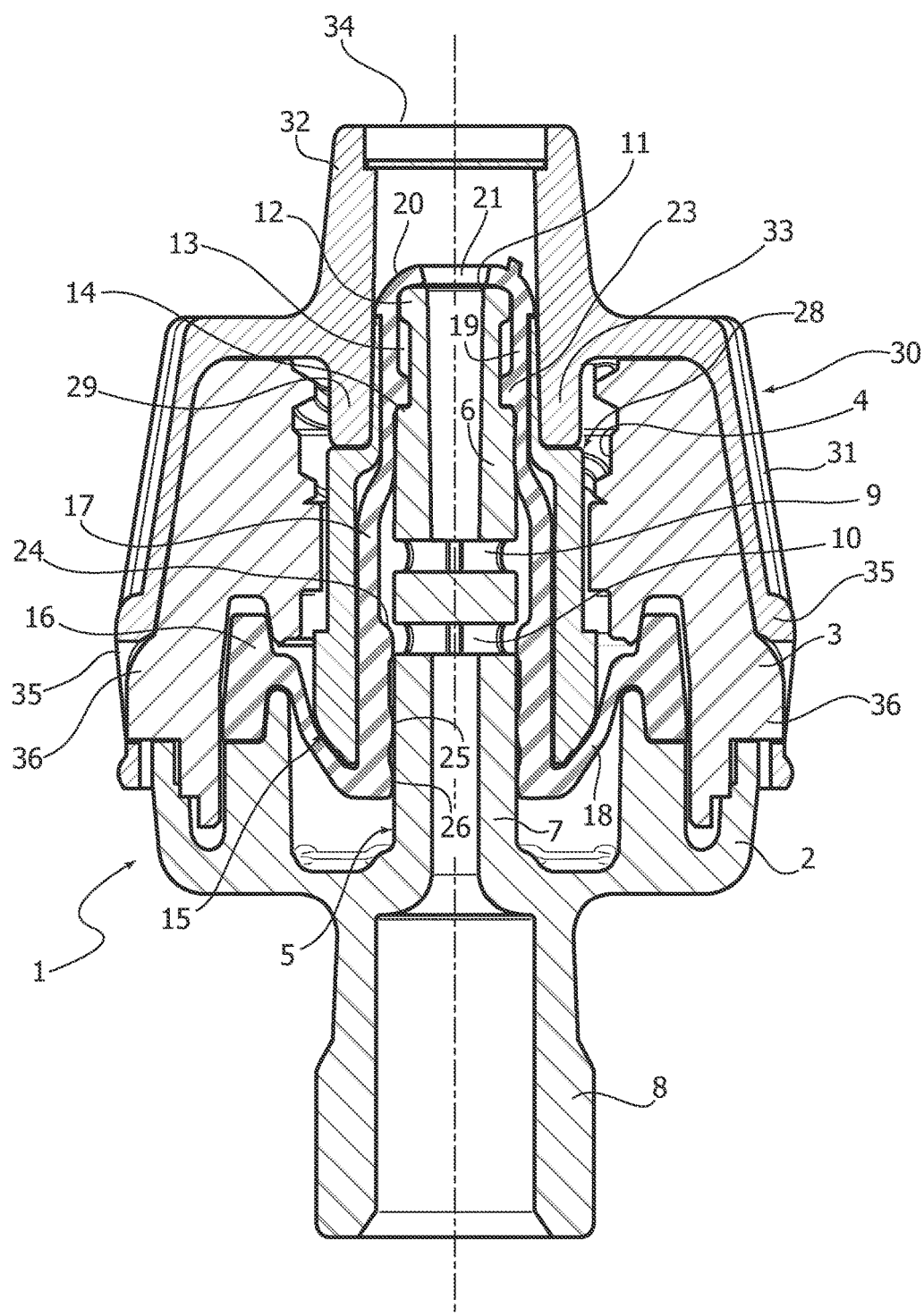
FIG. 5 is an analogous view to FIG. 2, which shows the valved connector in a second condition.

The skirt 31 of the priming cap 30 is selectively engageable with the casing 1, in a first axial position, represented in FIG. 2, or in a second axial position represented in FIG. 5. In the first position, the skirt 31 engages with the body 3, for example, by simple interference, essentially without interacting with the collar 28 and therefore without deforming the elastic hollow element 15. Therefore, in this first position, the valved connector remains closed and the priming cap 30 acts as a simple cover to protect the end wall 20 of the elastic hollow element 15.

In the second axial position represented in FIG. 5, the inner end part 33 of the priming cap 30 interacts with the step 29 of the collar 28, elastically deforming the elastic hollow element 15.

To arrange and stably maintain the priming cap 30 in the second axial position, two opposing slots 35 are formed at the base of the skirt 31, configured to cooperate with a complementary pair of radial projections 36 of the body 3 to achieve a rotation coupling of the bayonet type.

In this second axial position, as said, represented in FIG. 5, the priming cap 30 is secured to the body 3 due to the engagement of the slots 35 of the skirt 31 relative to the protrusions 36 of the body 3, under the elastic thrust applied by the elastic hollow element 15, displaying stretching deformation, against the step 29 of the collar 28.

Following the stretching deformation of the elastic element 15, the inner annular protrusion 24 of the elastic element 15 is arranged downwards, in order to free the communication between the radial passages 9 and 10 and therefore between the inlet 7 and the outlet 6 portions of the tubular member 5, while the cut 21 of the end wall 20 is simultaneously opened, thereby placing the end 11 of the outlet portion 6 of the tubular member 5 in communication with the outer tubular portion 32 of the priming cap 30. The tubular connector 8, and therefore the line connected to it during use, are thus maintained in communication with the atmosphere through the membrane 34 which, as said, constitutes an impermeable barrier to the medical liquid coming from the line.

In this way, the valved male luer connector according to the invention, without any risk of liquid loss, is ready for subsequent coupling with the female connector, without the need for further priming operations: it is in fact sufficient to remove the cap 30, disengaging the bayonet coupling 35-36, to then be able to apply the female connector in its replacement.

Of course, the details of construction of the embodiments may be widely varied with respect to those described and illustrated, without thereby departing from the scope of the present invention as defined by the following claims.

The invention claimed is:

1. A valved male luer connector comprising:
   a casing, a tubular member having an inlet portion and an outlet portion with an open terminal end,
   an elastic hollow element secured to the casing and enclosing the tubular member, said elastic hollow element having a terminal wall, which normally seals closed said terminal end of the outlet portion of the tubular member and having a cut,
   a collar interposed between the casing and the elastic hollow element and axially displaceable, following thrust engagement by a female connector connectable to said male connector, causing a stretching deformation of said elastic hollow element and consequent opening of the flow passage between said inlet portion and said outlet portion of the tubular member, and
   a priming cap releasably connectable to the casing of the connector to provide stretching deformation of said elastic element and to keep said terminal end of the outlet portion of the tubular member in communication with the atmosphere through a liquid-impermeable barrier,
   said priming cap comprising a skirt and a tubular part, said skirt arranged outside the casing and configured to engage said casing, said tubular part coaxial to said skirt,
   said tubular part comprising said liquid-impermeable barrier and said tubular part arranged to interact with said collar interposed between the casing and the elastic hollow element to cause said collar to move to contact said elastic hollow to deform said hollow element and allow fluid to flow from said inlet portion of said tubular member to said outlet portion of said tubular member to an interior of an outer tubular portion of said priming cap, said interior bounded by said liquid-impermeable barrier.

2. Valved connector according to claim 1, wherein said skirt of the priming cap can be selectively engaged with said casing in a first axial position to protect said terminal wall of the elastic hollow element, in which said elastic hollow element is essentially undeformed, and in a second axial position wherein said elastic hollow element is stretched, respectively.

3. Connector according to claim 2, wherein said skirt of the priming cap in said second axial position is connected to the casing of the connector by means of a bayonet coupling.

4. Connector according to claim 1, wherein said liquid-impermeable barrier consists of a hydrophobic membrane.

5. Connector according to claim 2, wherein said liquid-impermeable barrier consists of a hydrophobic membrane.

6. Connector according to claim 3, wherein said liquid-impermeable barrier consists of a hydrophobic membrane.

* * * * *